United States Patent
Varma et al.

(10) Patent No.: US 12,146,684 B2
(45) Date of Patent: Nov. 19, 2024

(54) AIR CLEANING APPARATUS

(71) Applicant: V3 Corporation, Lewis Center, OH (US)

(72) Inventors: Vivek Varma, Lewis Center, OH (US); Vijaysimha Ajarananda, Bangalore (IN)

(73) Assignee: V3 Corporation, Lewis Center, OH (US)

( * ) Notice: Subject to any disclaimer, the term of this patent is extended or adjusted under 35 U.S.C. 154(b) by 301 days.

(21) Appl. No.: 17/548,892

(22) Filed: Dec. 13, 2021

(65) Prior Publication Data

US 2022/0186952 A1 Jun. 16, 2022

(30) Foreign Application Priority Data

Dec. 11, 2020 (IN) .............................. 202011054040

(51) Int. Cl.
*F24F 8/22* (2021.01)
*F24F 8/108* (2021.01)
*F24F 8/192* (2021.01)

(52) U.S. Cl.
CPC ............... *F24F 8/22* (2021.01); *F24F 8/108* (2021.01); *F24F 8/192* (2021.01)

(58) Field of Classification Search
CPC ... F24F 8/22; F24F 8/108; F24F 8/192; A61L 2209/14; A61L 9/205; A61L 9/22; Y02A 50/2351
See application file for complete search history.

(56) References Cited

U.S. PATENT DOCUMENTS

| | | | | |
|---|---|---|---|---|
| 5,294,315 A * | 3/1994 | Cooper | .................... | B01J 35/00 |
| | | | | 204/158.21 |
| 5,875,384 A * | 2/1999 | Peill | ........................ | C02F 1/325 |
| | | | | 422/186 |
| 5,993,738 A * | 11/1999 | Goswani | .................. | B03C 3/60 |
| | | | | 422/4 |
| 6,187,271 B1 * | 2/2001 | Lee | ........................ | B03C 3/016 |
| | | | | 96/225 |
| 6,241,856 B1 * | 6/2001 | Newman | .................. | B01J 35/39 |
| | | | | 204/157.3 |
| 6,309,611 B1 * | 10/2001 | Tabatabaie-Raissi | .... | B01J 35/30 |
| | | | | 422/186 |

(Continued)

FOREIGN PATENT DOCUMENTS

JP     2005016841 A     1/2005

OTHER PUBLICATIONS

The International Search Report and Written Opinion issued in corresponding PCT Application No. PCT/US2021/063047; Mailing Date: Feb. 24, 2022.

*Primary Examiner* — David A Vanore
(74) *Attorney, Agent, or Firm* — Pearne & Gordon LLP

(57) ABSTRACT

An air cleaning apparatus includes a fan assembly configured to induce a vortex extending in front of the air cleaning apparatus for extracting air from a targeted region to remove and inactivate airborne pathogens (e.g., viruses) in the air. The air cleaning apparatus includes a reactor core configured to inactivate airborne pathogens via contact with anatase coated plates activated by UVC light. The air cleaning apparatus includes a filter assembly for removing reactive oxygen species in the decontaminated air.

9 Claims, 12 Drawing Sheets

(56) References Cited

U.S. PATENT DOCUMENTS

| | | | | |
|---|---|---|---|---|
| 6,752,957 B1* | 6/2004 | De Lasa | | B01D 53/007 |
| | | | | 422/186.3 |
| 6,843,835 B2* | 1/2005 | Fornai | | B01D 50/60 |
| | | | | 96/240 |
| 7,147,692 B2* | 12/2006 | Fornai | | B01D 47/06 |
| | | | | 96/290 |
| 7,820,100 B2* | 10/2010 | Garfield | | B01J 35/39 |
| | | | | 423/403 |
| 8,309,484 B2* | 11/2012 | Hugener-Campbell | | |
| | | | | B01J 35/39 |
| | | | | 502/232 |
| 8,328,917 B2* | 12/2012 | Garfield | | F24F 8/167 |
| | | | | 424/688 |
| 9,855,362 B2 | 1/2018 | Engelhard | | |
| 11,524,090 B1* | 12/2022 | Wagner | | A61L 9/014 |
| 2002/0170815 A1* | 11/2002 | Fujii | | B01D 53/007 |
| | | | | 422/186.3 |
| 2003/0056648 A1* | 3/2003 | Fornai | | B01D 50/60 |
| | | | | 95/149 |
| 2004/0007453 A1* | 1/2004 | Scahill | | B01D 53/885 |
| | | | | 422/186.3 |
| 2004/0241040 A1* | 12/2004 | Wei | | B01J 21/063 |
| | | | | 422/4 |
| 2005/0159309 A1* | 7/2005 | Hubbell | | E01F 15/0423 |
| | | | | 502/439 |
| 2005/0263003 A1* | 12/2005 | Fornai | | F24F 8/133 |
| | | | | 95/211 |
| 2008/0286163 A1* | 11/2008 | Garfield | | A61L 9/205 |
| | | | | 427/532 |
| 2009/0010801 A1 | 1/2009 | Murphy et al. | | |
| 2009/0041632 A1* | 2/2009 | Day | | A61L 9/205 |
| | | | | 422/121 |
| 2010/0260644 A1* | 10/2010 | Day | | A61L 9/205 |
| | | | | 29/527.4 |
| 2011/0030560 A1 | 2/2011 | Bohlen et al. | | |
| 2011/0100221 A1 | 5/2011 | Wu | | |
| 2011/0150720 A1* | 6/2011 | Garfield | | B01J 35/56 |
| | | | | 422/186.3 |
| 2012/0121470 A1* | 5/2012 | Morito | | B01D 53/885 |
| | | | | 422/121 |
| 2018/0185785 A1* | 7/2018 | Fava | | B01D 53/323 |
| 2019/0120508 A1* | 4/2019 | Goswami | | F24F 8/80 |
| 2019/0167832 A1 | 6/2019 | Lee et al. | | |
| 2020/0030731 A1* | 1/2020 | Dhau | | B01D 53/0407 |
| 2020/0109869 A1* | 4/2020 | Mäkipää | | B03C 3/47 |
| 2020/0179945 A1 | 6/2020 | Makipaa et al. | | |
| 2020/0353424 A1* | 11/2020 | Ale Ebrahim | | B01D 69/02 |
| 2021/0236682 A1* | 8/2021 | Willette | | B01D 46/10 |
| 2022/0186952 A1* | 6/2022 | Varma | | A61L 9/205 |
| 2022/0362713 A1* | 11/2022 | Cai | | B01J 35/39 |

\* cited by examiner

AIR CLEANING APPARATUS

CROSS REFERENCE TO RELATED APPLICATIONS

This application claims priority to, and any other benefit of Indian Application Serial No. 202011054040, filed Dec. 11, 2020, the entire disclosure of which is incorporated herein by reference as though recited herein in its entirety.

FIELD OF THE INVENTION

The present invention relates to an air cleaning apparatus, and more particularly, an apparatus for extracting and sanitizing air in a targeted area to remove and inactivate airborne pathogens (e.g., viruses) therefrom.

BACKGROUND

The infectivity of aerosolized viruses, such as SARS-COV-2 aerosols, is an area of active research with far reaching implications on exposure and disease transmission. Though the minimal concentration of virus in aerosolized samples is variable, and the amount of virus required to cause disease, such as COVID-19 and its many variants, is dependent on many factors including host immunity, at least one study shows that simply using PPE does not eliminate risk for healthcare providers. Furthermore, studies analyzing air samples from hospitals have identified live viruses in areas where aerosol generating procedures are not performed (e.g., hospital rooms, changing facilities, waiting areas and hallways). This indicates that the transmission risk of aerosolized virus is much higher than expected. The implications of aerosol spread to doctors and nurses are wide reaching and include a significant risk of transmitting disease to other patients, thus increasing the rate of hospital acquired infections.

Current air handling systems, including negative pressure rooms in ICU/Wards and hospital waiting rooms, are inadequate for containing the viral loads. In addition, they are cumbersome to set up and are costly. HEPA filters provide filtered air into the room but do not effectively clear out pathogens generated by the sickest patients in a closed room. Additionally, they do not sanitize the air, nor are they configured to remove air from the area of highest transmission, which is generally an area immediately surrounding a patient. This inability to precisely control air extraction is even shared by competing technologies using photon emission or cold plasma emission which neutralize the virus that enters their system but does not solve the problem of limiting its spread in an enclosed space.

BRIEF SUMMARY

The following presents a simplified summary in order to provide a basic understanding of the embodiments described herein. This summary is not an extensive overview, nor is it intended to identify key or critical elements. Its sole purpose is to present some concepts in a simplified form as a prelude to the more detailed description that is presented later.

According to an example embodiment, an air cleaning apparatus includes a housing; a fan configured to extract an airstream from a targeted area into the housing; and a reactor core positioned within the housing, the reactor core comprising one or more technologies to extract and neutralize pathogens in the airstream, the technologies comprising electrostatic precipitation, ultraviolet radiation, photocatalytic oxidation, and filtration.

BRIEF DESCRIPTION OF DRAWINGS

Throughout the drawings and the detailed description, unless otherwise described, the same drawing reference numerals can be understood to refer to the same elements, features, and structures. The relative size and depiction of these elements may be exaggerated for clarity, illustration, and convenience.

DETAILED DESCRIPTION OF INVENTION

Figure 1:
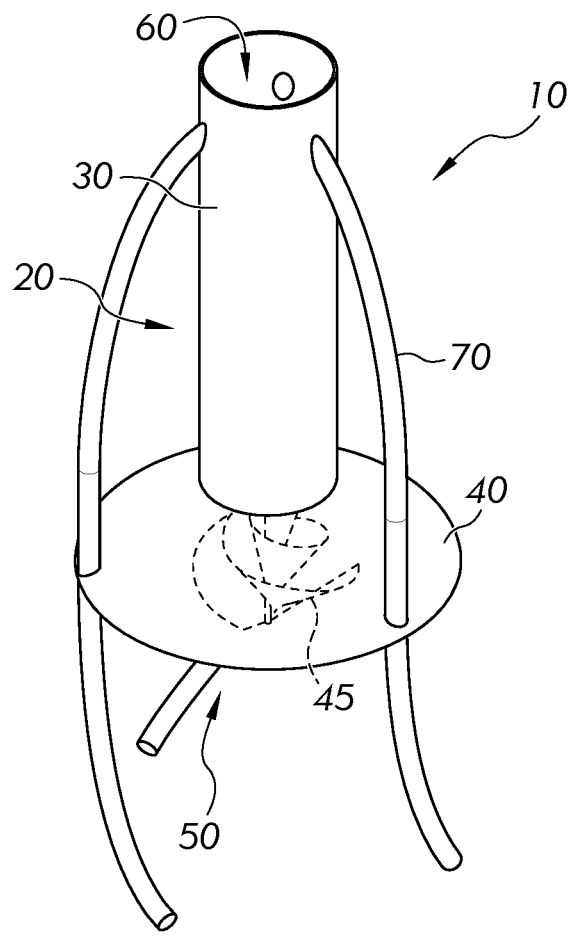
FIG. 1 illustrates a perspective view of an example air cleaning apparatus in accordance with a first embodiment.

Example embodiments are described and illustrated herein. These illustrated examples are not intended to be a limitation on the present embodiments. For example, one or more aspects of the system can be utilized in other embodiments and other types of air cleaning systems. Example embodiments of an air cleaning apparatus will be described more fully hereinafter with reference to the accompanying drawings. Such systems may, however, be embodied in many different forms and should not be construed as limited to the embodiments set forth herein. Like, but not necessarily the same, elements in the various figures are denoted by like reference numerals for consistency. Terms such as "first," "second," "front," and "rear" are used merely to distinguish one component (or part of a component or state of a component) from another. Such terms are not intended to denote a preference or a particular orientation.

Referring initially to FIG. 1, an example air cleaning apparatus 10 is illustrated in accordance with a first embodiment. The air cleaning apparatus 10 can be a portable system that allows removal and sterilization of infected air. For instance, the air cleaning apparatus 10 can be used to maintain sterility in hospitals, operating rooms, medical or dental clinics and various other commercial businesses. The air cleaning apparatus 10 includes a housing 20 having a main body 30 coupled to a skirt portion 40, which functions as a housing for a fan 45. The main body 30 can have a generally cylindrical configuration, as shown. However, it is to be appreciated that the housing 20 can include any suitable configuration as desired. The skirt portion, or fan housing, 40 defines an air inlet 50 for receiving contaminated air into the air cleaning apparatus 10. An air outlet 60 is positioned at an end of the main body 30 through which cleaned and sterilized air can exit.

Figure 5:
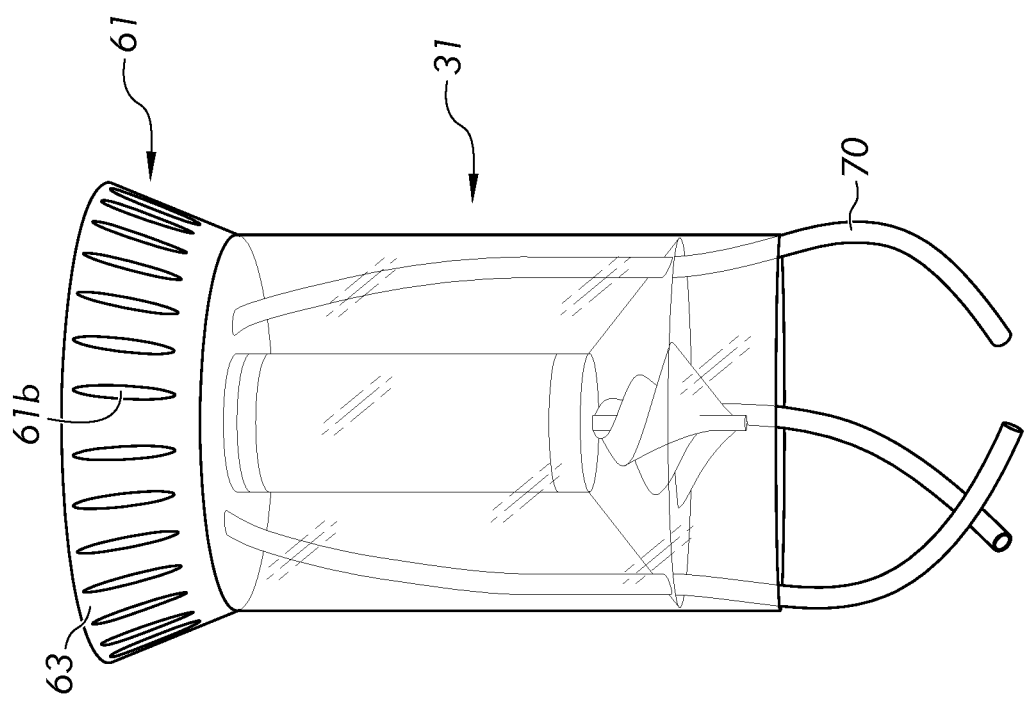
FIG. 5 illustrates a perspective view of an air cleaning apparatus with an outer housing shown in a transparent view in accordance with an example embodiment.
Figure 6:
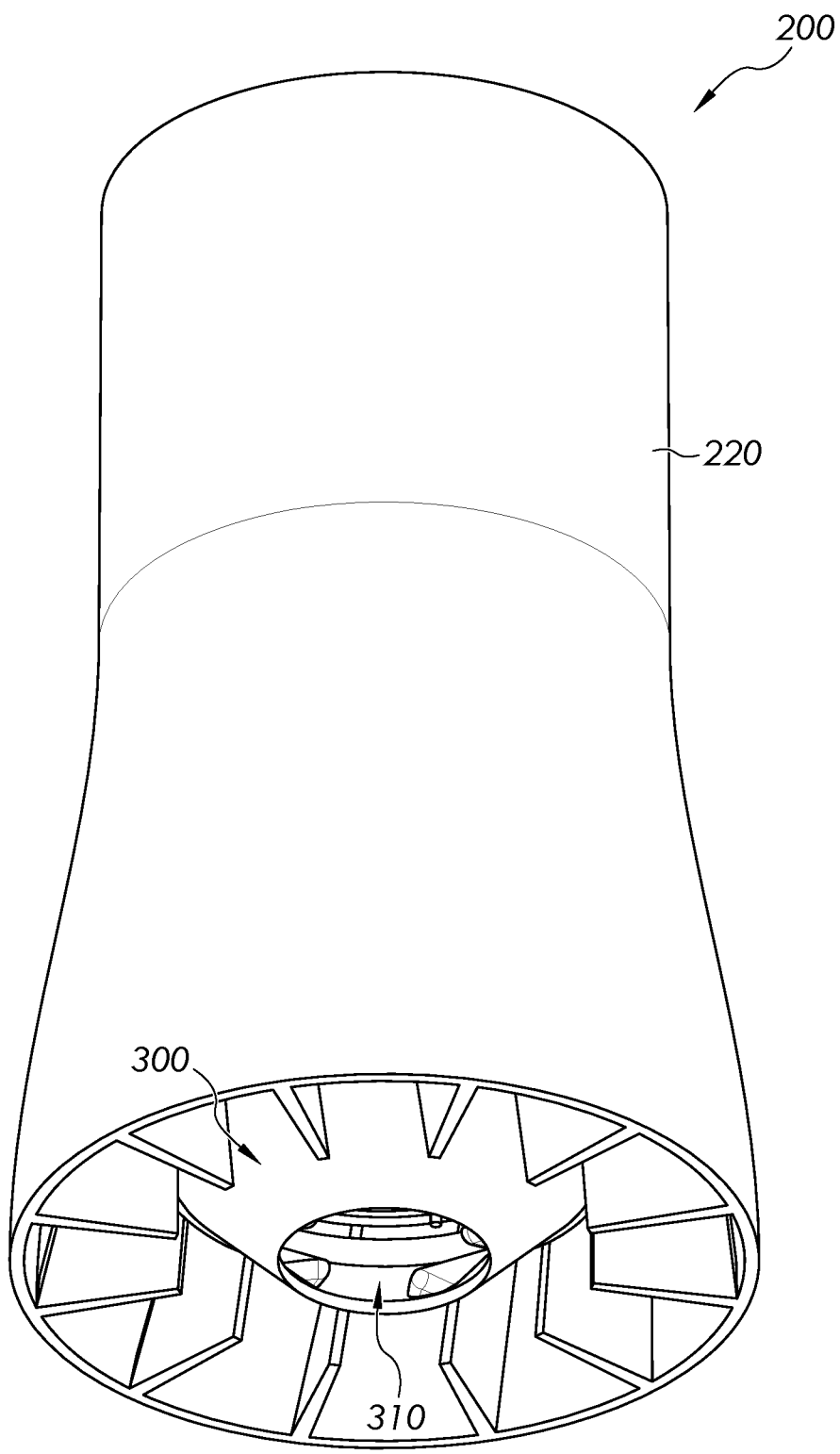
FIG. 6 illustrates a perspective view of an example air cleaning apparatus in accordance with a second embodiment.

Referring to FIG. 5, in some embodiments, the air cleaning apparatus 10 may include an external shroud 31 enclosing the housing 20 (FIG. 1) to make the air cleaning apparatus 10 aesthetically more pleasing in fit and finish. Additionally, the external shroud 31 serves to protect air conduits 70 extending from an outlet 60 (FIG. 1) of the air cleaning apparatus 10 toward the inlet 50 (FIG. 1) thereof. In some embodiments, a cap 61 may be attached to an upper end of the external shroud 31 to enclose the air outlet 60. In such embodiments, the cap 61 may define a plurality of air egress openings 61b for enabling sanitized air to be expelled from the air cleaning apparatus 10. In the illustrated embodiment, the cap 61 is a conical-shaped structure including egress openings 61b that are substantially elliptical shaped. In particular, the cap includes a sloped or angled outer wall 63 with a diameter that decreases from an upper end thereof to a lower end thereof proximate a junction of the cap 61 and the external shroud 31. In this embodiment, the angled outer wall 63 facilitates directing air exiting the egress openings 61b to be directed downward, thereby creating an envelope of clean or sanitized air around air suctioned in the air inlet 50 (FIG. 1) of the air cleaning apparatus 10. Advantageously, this envelope of clean or sanitized helps mitigate exposure to contaminated air suctioned into the air cleaning apparatus 10 through the air inlet 50 (FIG. 1) thereof, e.g., for protecting medical personnel or patients from being exposed to contaminated air suctioned into the air cleaning apparatus. The portability and configuration of the air cleaning apparatus 10 allows it to be positioned adjacent to an area having a highest concentration of infectious aerosols, such as near or above an infected patient, to draw air directly into the housing 20 where the air is cleaned and sterilized.

Figure 2:
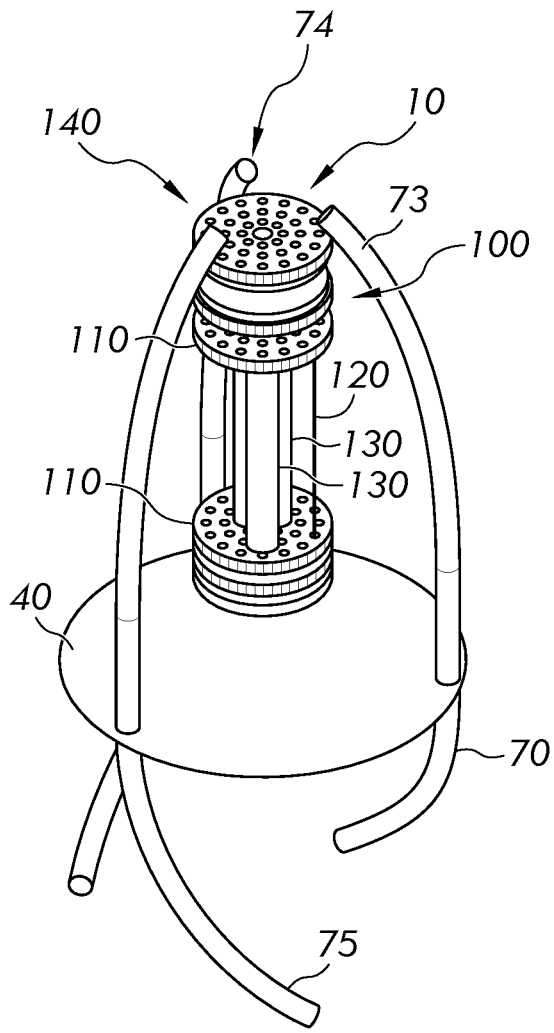
FIG. 2 illustrates a perspective view of an air cleaning apparatus with an outer housing removed in accordance with an example embodiment.
Figure 4:
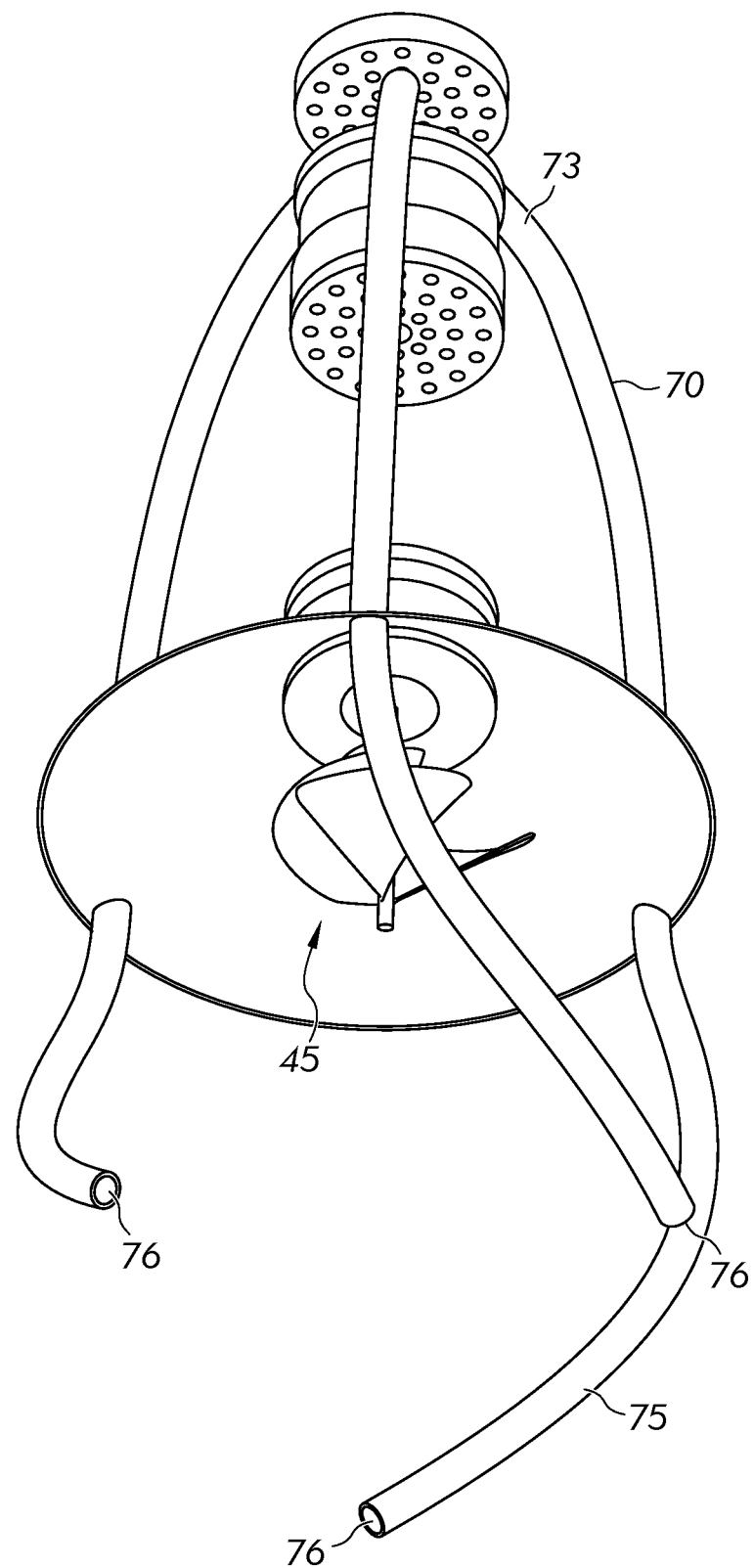
FIG. 4 illustrates a perspective view of an air cleaning apparatus with a portion of a reactor core and outer housing removed in accordance with an example embodiment.

Referring to FIG. 1, the air inlet 50 and air outlet 60 can be positioned on opposing ends of the housing 20. One or more air conduits 70 can be coupled to the housing 20 to facilitate seeding of a vortex external to the air intake to facilitate efficient air flow and targeted extraction. Referring to FIG. 2, the air conduits 70 each include a first end portion 73 that is angled towards a top portion of the housing 20 to receive cleaned air. For example, each first end portion 73 can be angled between 45-degrees and 75-degrees towards the housing 20. Air received from the air outlet 60 then travels through a first opening 74 in the first end portion 73, and downwards through the air conduits 70 to a second end portion 75. The air then exits a second opening 76 (FIG. 4) in the second end portion 75 to an area below the fan 45. (FIG. 4) In the illustrated embodiment, the second end portions 75 are skewed (e.g., at an acute angle, for example 45 degrees). This orientation causes air exiting the second openings 76 to generate a vortex below a fan impeller, as will be described in greater detail below, and with the friction, will develop a vortex that extends to the ground or to a predetermined area. It should be appreciated that the specific orientation and angle of the second end portions 75 may differ from that which is shown without departing from the scope of the present disclosure. For instance, in some embodiments, the angle may be different from what is shown.

Turning now to FIG. 2, the example air cleaning apparatus 10 is illustrated with the main body 30 of the housing 20 (FIG. 1) removed. The components housed within the main body 30 constitutes a reactor core 100 comprising a plurality of stacked technologies for improved air decontamination. The fan 45 (FIG. 4) is positioned at the air inlet 50 and is configured to pull air from the environment into the reactor core 100. In addition, the reactor core 100 includes an electrostatic precipitator comprising at least one, and preferably, two or more metal plates 110 and at least one ionizer 120 extending between the two or more metal plates 110. For example, first and second plates 110 are generally parallel to each other and a first end portion of the ionizer(s) 120 can be bonded to a separate fixture adjacent to the first plate and a second end portion of the ionizer(s) 120 can be bonded to a fixture adjacent to the second plate, such that the ionizer(s) 120 extends substantially perpendicularly between the first and second plates 110. As infected air travels into the reactor core 100, a high DC voltage, such as 15 KV for example, is applied to the ionizer(s) 120, which acts to charge pathogens in the air stream, which are then attracted to the metal plates 110. During this process, the pathogens are inactivated by the charge and/or trapped by the plates 110. The size of the plates, length of the discharge electrode, and amount of voltage applied varies based on the size of the air cleaning apparatus 10 and the size of the area to be disinfected.

The plates 110 are coated with a layer of titanium dioxide ($TiO_2$) nano structure (anatase), which absorbs light and promotes a chemical reaction. One or more ultraviolet (UV) lamps 130, such as UV-C lamps, extend between the plates 110. As the $TiO_2$ coating absorbs ultraviolet rays, a photocatalytic oxidation reaction occurs to inactivate and neutralize the charged pathogens as they contact the plates 110, thereby further reducing microorganisms, such as bacteria, viruses, spores, organic compounds, and pathogens. Additionally, the UV-C light from the lamps 130 can irradiate and destroy any remaining pathogens on surfaces and in the air. During the described air cleaning and sanitizing process, ozone gas is typically generated. Excessive amounts of ozone gas can cause irritation to patients, particularly to breathing passages. Accordingly, near the air outlet 60, a filter or filter assembly 140 is provided to remove or destroy ozone from the airstream. Such a filter assembly 140 can include a material made of Ag/Cu wool or the like to remove ionized air particles and reactive oxygen species (ROS) from the air passing through the filter 140.

Thus, the air cleaning apparatus 10 can work as a stand-alone air treatment reactor and includes sequentially stacked, validated pathogen neutralizers that actively extract and neutralize airborne pathogens in four stages:

Stage 1: Ionizes pathogens entering the stack using a high DC voltage ionizer cable.

Stage 2: The charged pathogens are attracted to the anode of the precipitator plates coated with a layer of titanium dioxide nano structure (anatase) and photoactivated by an environment of UV-C light that instantly inactivates and neutralizes the charged pathogens as they contact the plate for a high degree (up to an estimated log 4) reduction in virus.

Stage 3: The pathogens that escape the Electrostatic Precipitator Layer are further immersed in an environment of UV-C light and which has a proven log 3 reduction of sample viruses.

Stage 4: An outlet filter made of Ag/Cu wool grounded to remove traces of ionized air particles and other ROS (ozone and peroxides) before releasing the air back into the room.

Figure 3:
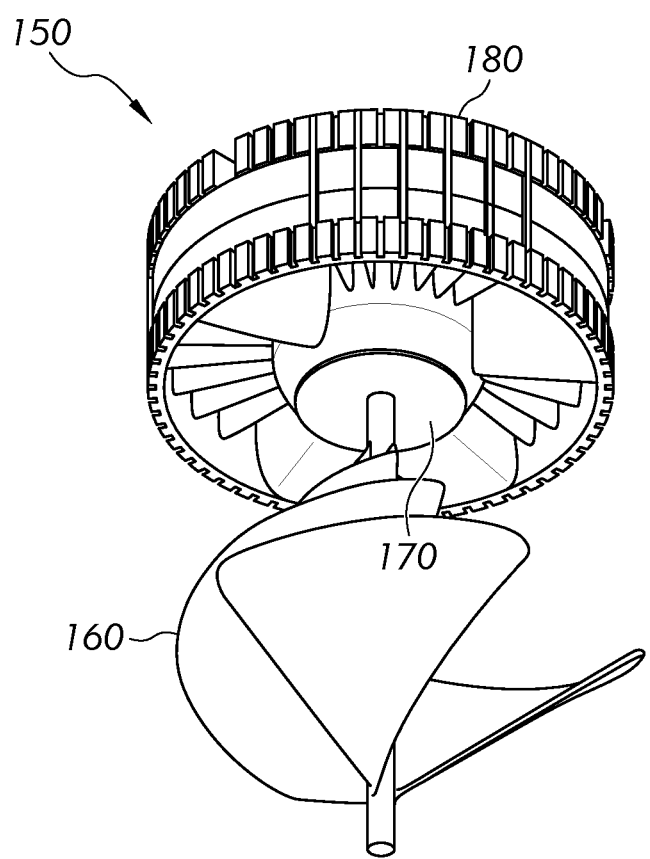
FIG. 3 illustrates a fan design for an air cleaning apparatus in accordance with an example embodiment.

Turning now to FIG. 3, an example fan assembly 150 for use with an air cleaning apparatus is illustrated in accordance with an embodiment. The fan assembly 150 is configured to extract air from a targeted area by creating a vortex or "tornado" of negative pressure above the targeted area, such as an area surrounding one or more patients. The extracted air is then directed into the reactor core 100 for cleaning. The fan assembly 150 includes a low noise impeller 160, which can be operated by a brushless DC motor 170 and coupled to the air cleaning apparatus via a spoke mount with vibration dampers 180. The configuration of the fan impeller 160 allows a negative pressure vortex to be created in a targeted area, such as around a patient, of highest infectivity. Thus, as compared to conventional air cleaning systems which rely on laminar airflow modeling for general air cleaning in an enclosed space, such as a hospital room, the present air cleaning apparatus can specifically target an area of highest infectivity to direct more of the infected air into the reactor core. For example, the air cleaning apparatus can be positioned near an infected patient's mouth/nose/face. This positioning coupled with the type of fan employed, allows the fan assembly 150 to extract at least 3.5 times and preferably, up to 5 times more of the infected air in a space than conventional systems, as such systems do not target or pull in airstreams from areas with a highest concentration of pathogens. In the fan assembly 150, air is pulled into the housing 20 and through reactor core 100 by the impeller 160, which is a modified 3 blade Archimedes impeller/turbine adapted to efficiently provide air suction with minimal noise generation due to air friction. It can generate a higher Froude number compared to other standard axial fan designs because of the continuous and large blade surfaces that comprise it. The impeller can be made from Tungsten Inert Gas (TIG) welded titanium sheet metal or of formed carbon fiber reinforced structure. A special surface texture on either side of the blades of the impeller generates interfacial vortices that reduce friction and enhance power input efficiency.

The shape, design and increased surface area of the blades allow for concentrated and efficient extraction and greater air movement compared to that from traditional fan blades or vortex type systems, which only create vortexes within their system confines. The fan is designed to withstand high speeds (up to 30,000 rpm). The combination of the fan materials and unique design maximizes air flow into the system while minimizing collateral air spread or drag. The dimensions of the fan have been specified to maximize pathogen contact time with collector plates given pathogen particle size, intake air flow rate and residence time within the reactor core.

Once contaminated air is moved into the reactor core, the air hits the electrostatic precipitator and nano-coating, which kills the pathogens. The air then exits the first part of the reactor core and into the second portion where it undergoes direct UV light radiation. However, prior to entering the second portion of the reactor core (UV lamps), a portion of the air is recirculated back into the first part of the reactor core. This is done utilizing tubes that divert, the air leaving the end of the first part of the reactor core (collector plates and ESP) back into it again for another pass at the collector plates. Therefore, pathogens are run through multiple cycles of deactivation to make sure a negligible amount escapes into the second portion of the reactor core.

Referring now to FIGS. 6 through 13, an air cleaning apparatus 200 according to a second embodiment will now be described. The air cleaning apparatus 200, in general, includes an outer shroud 220, a reactor core 400, an inner shroud 470, and a fan assembly 500.

Figure 7:
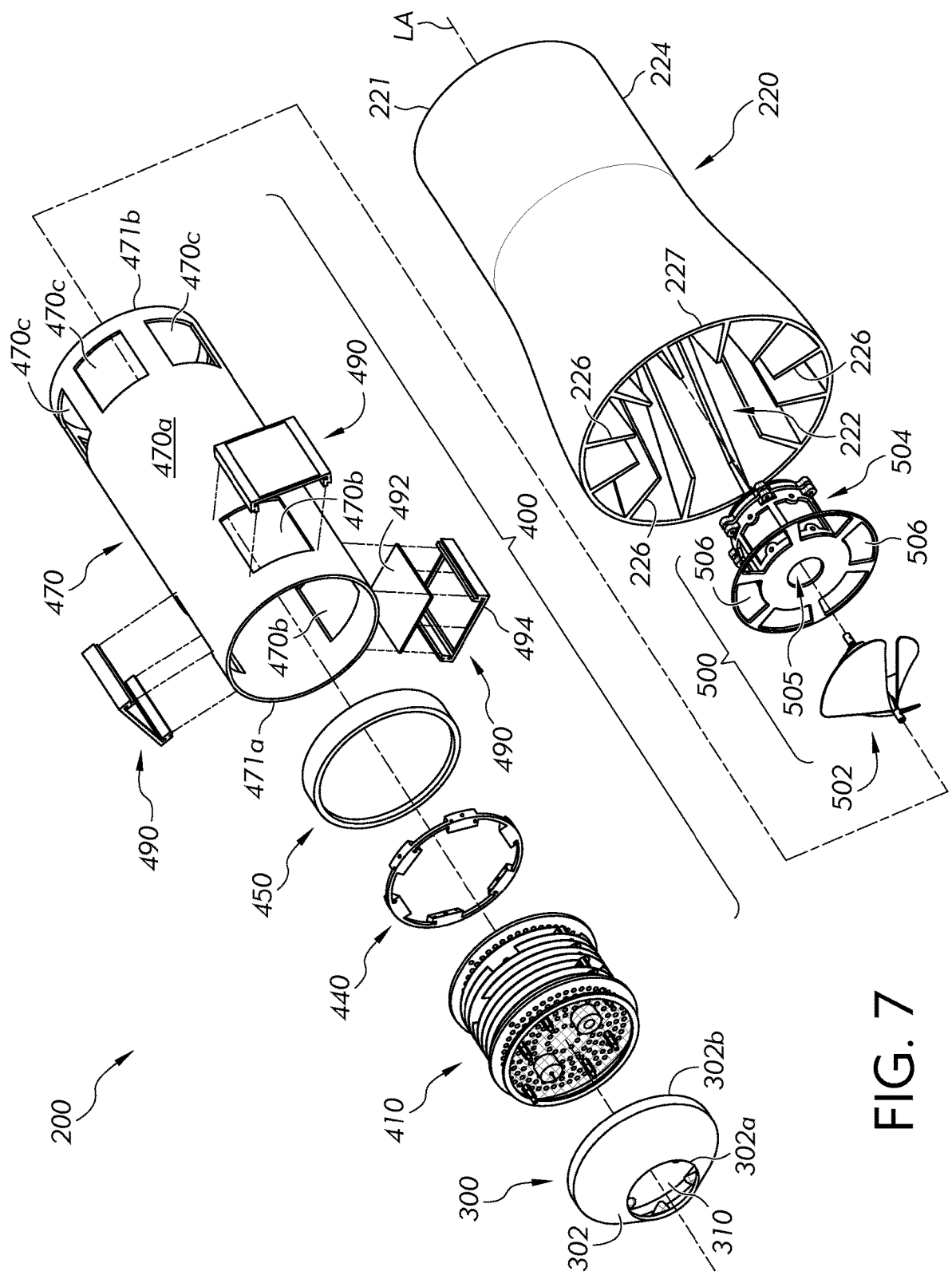
FIG. 7 illustrates an exploded, perspective view of the air cleaning apparatus of FIG. 6 in accordance with an example embodiment.
Figure 8:
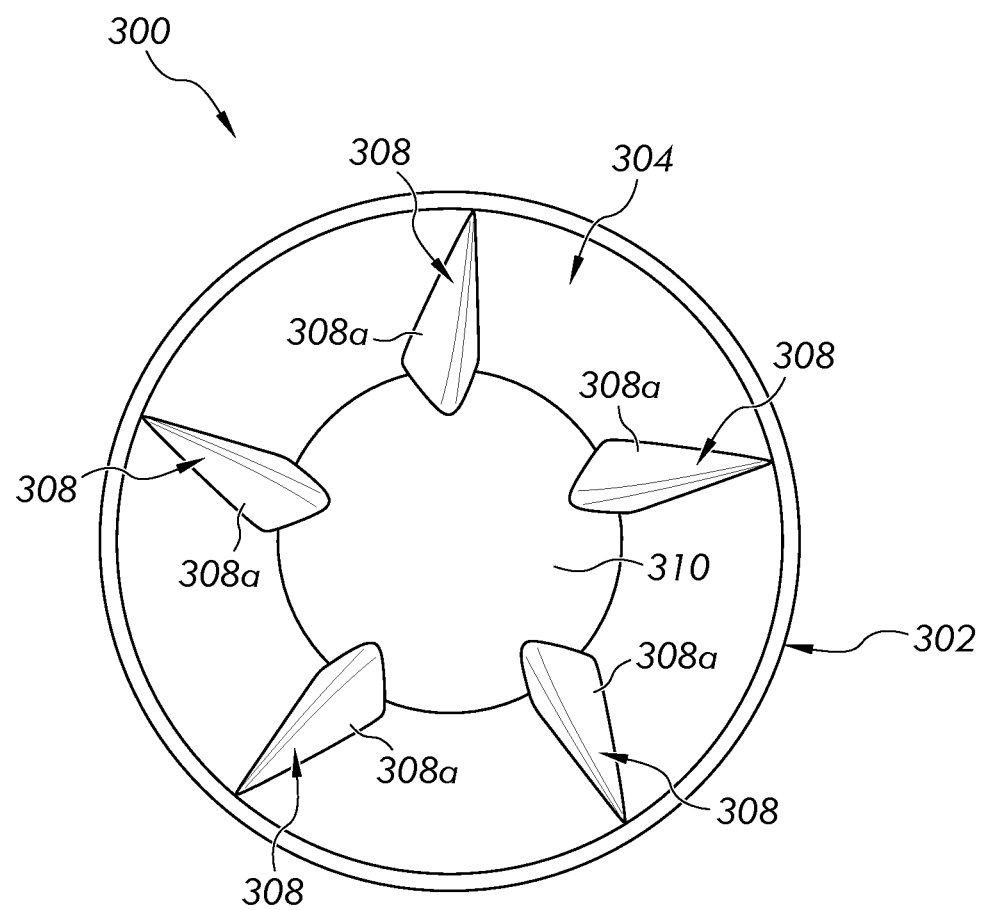
FIG. 8 illustrates a rear view of an air intake for an air cleaning apparatus in accordance with an example embodiment.

As shown in FIGS. 7 and 8, an air intake 300 is mounted at a first or forward end 471a of the inner shroud 470. The air intake 300 includes a body 302 with a first end 302a and a second end 302b. The first end 302a defines an air inlet 310 for receiving contaminated air that is extracted from an external environment, e.g., a targeted region or space. In the illustrated embodiment, the body 302 is substantially conical such that its diameter generally decreases from the second end 302b thereof to the first end 302a thereof. However, it is contemplated that the air intake 300 may take on other suitable shapes and forms for receiving contaminated air.

Referring to FIG. 8, the air intake 300 defines an inner surface 304 including a plurality of baffles 308 (for inducing turbulence) integrally formed thereon. It is contemplated that the baffles 308 may be molded, adhered, or welded to the inner surface 304 of the air intake 300. In other embodiments, it is contemplated that the baffles 308 may be removably mounted to the inner surface 304, for example, via removable fasteners and the like.

Specifically, the baffles 308 are configured to direct air passing through the air inlet 310 toward an opening 424 (FIG. 9) formed in a leading plate 421a (FIG. 9) of an electrostatic precipitator (ESP) plate assembly 410 (FIG. 9), as discussed in detail below. In the illustrated example, the baffles 308 each include a sloped surface 308a configured to generate a spiral air flow pattern inside the inner shroud 470 (FIG. 7), as discussed in detail below. It is noted that generating a spiral air flow pattern in this manner improves airflow efficiency in the inner shroud 470, thereby creating a homogenous distribution of particulates present in the air stream.

Figure 11:
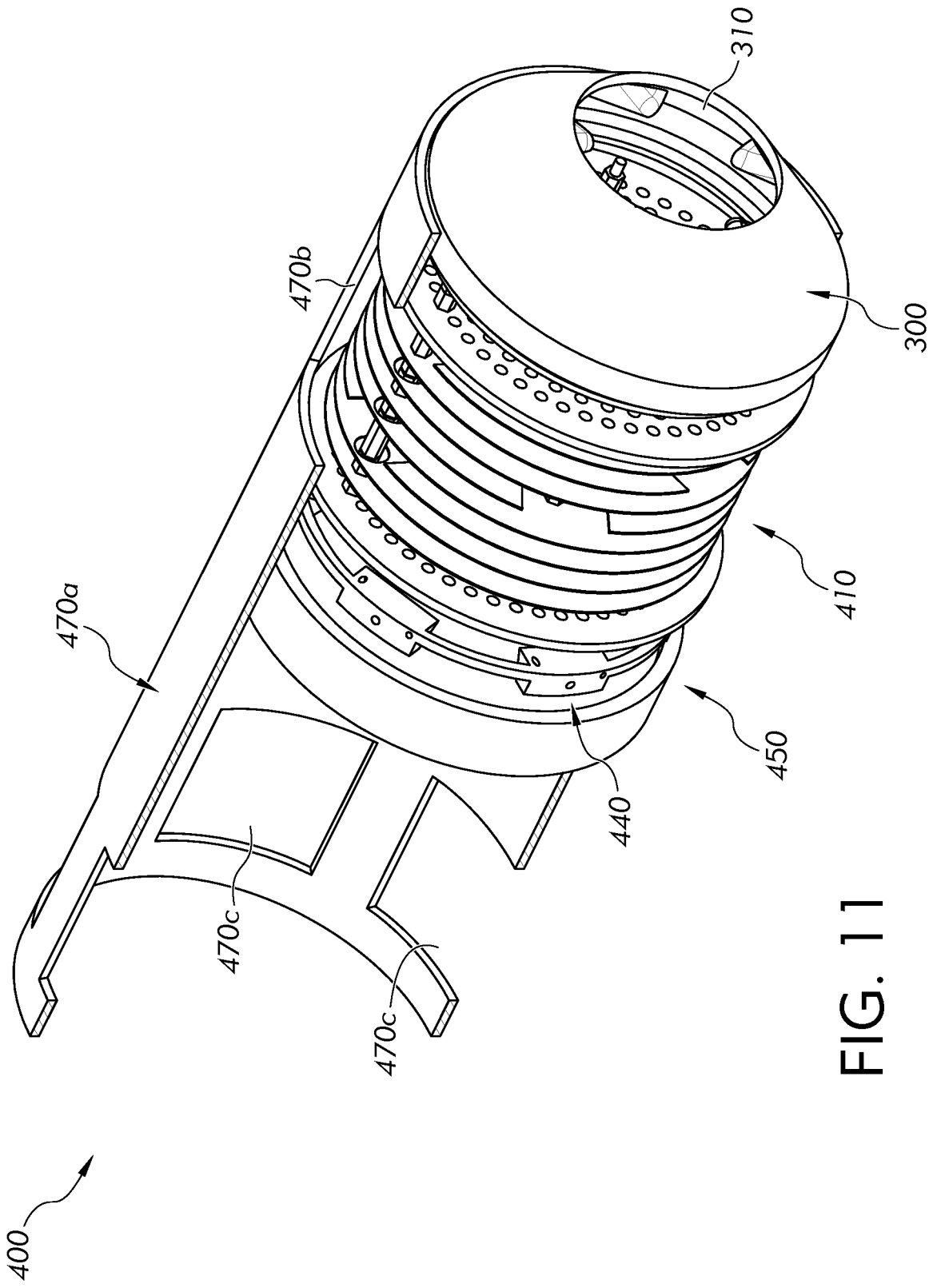
FIG. 11 illustrates a sectioned, perspective view of an inner shroud shown with an electrostatic precipitator assembly, a LED ring, and a filter assembly in accordance with an example embodiment.

Referring to FIGS. 7 and 11, the reactor core 400, in general, is configured to decontaminate air passing through the inner shroud 470 of the air cleaning apparatus 200. In the illustrated embodiment, the reactor core 400 is bounded by the inner shroud 470 and includes an ESP plate assembly 410 and a LED ring 440. A filter assembly 450 is disposed behind the LED ring 440 for removing residual reactive oxygen species (ROS) in the air before the air exits egress openings 470c of the inner shroud 470. In addition, the reactor core 400 includes a plurality of UV-C light assemblies 490 (FIG. 7) removably mounted to an outer surface of the inner shroud 470. Each of these components, will now be discussed in greater detail.

Figure 9:
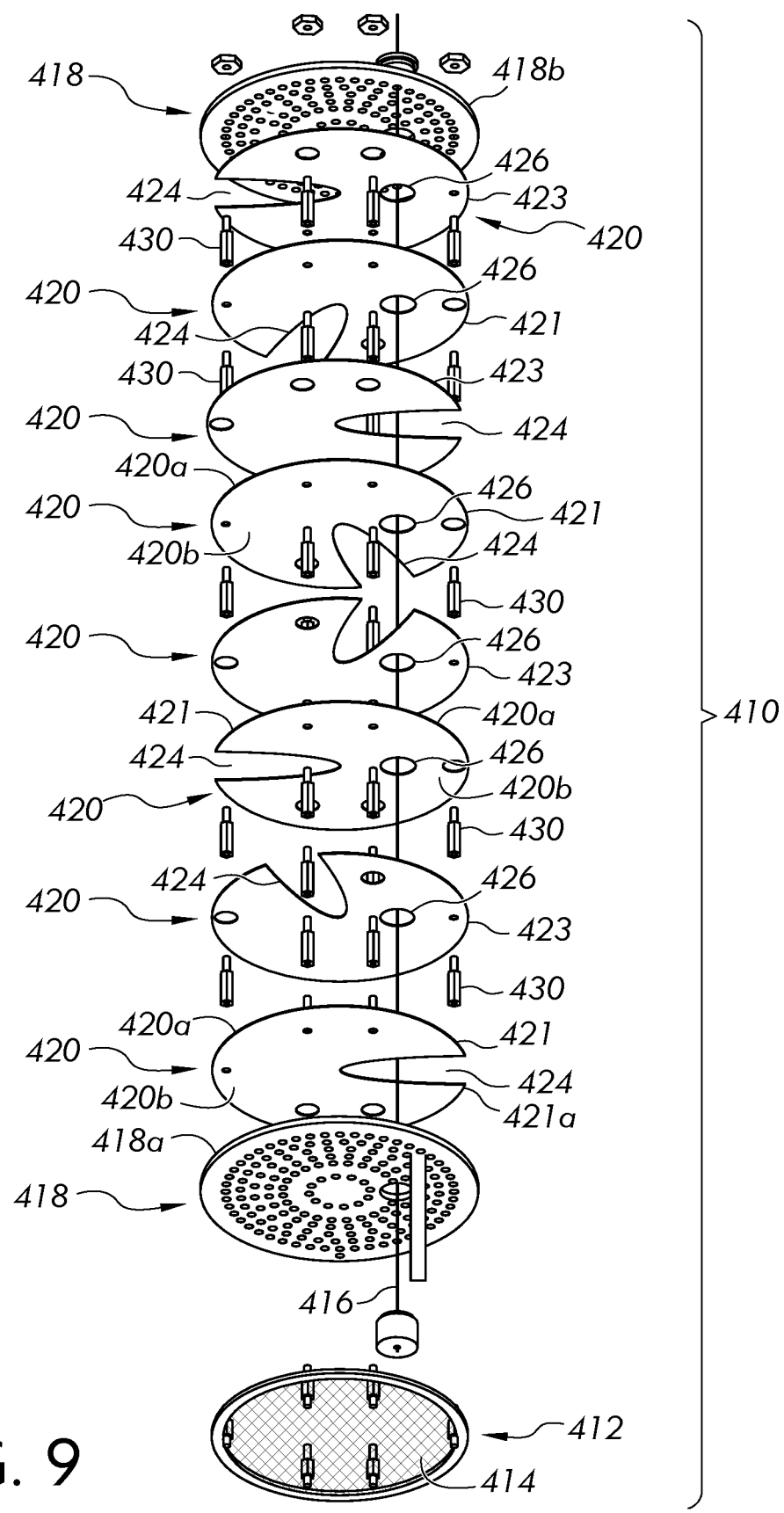
FIG. 9 illustrates an exploded, perspective view of an electrostatic precipitator assembly for an air cleaning apparatus in accordance with an example embodiment.
Figure 10:
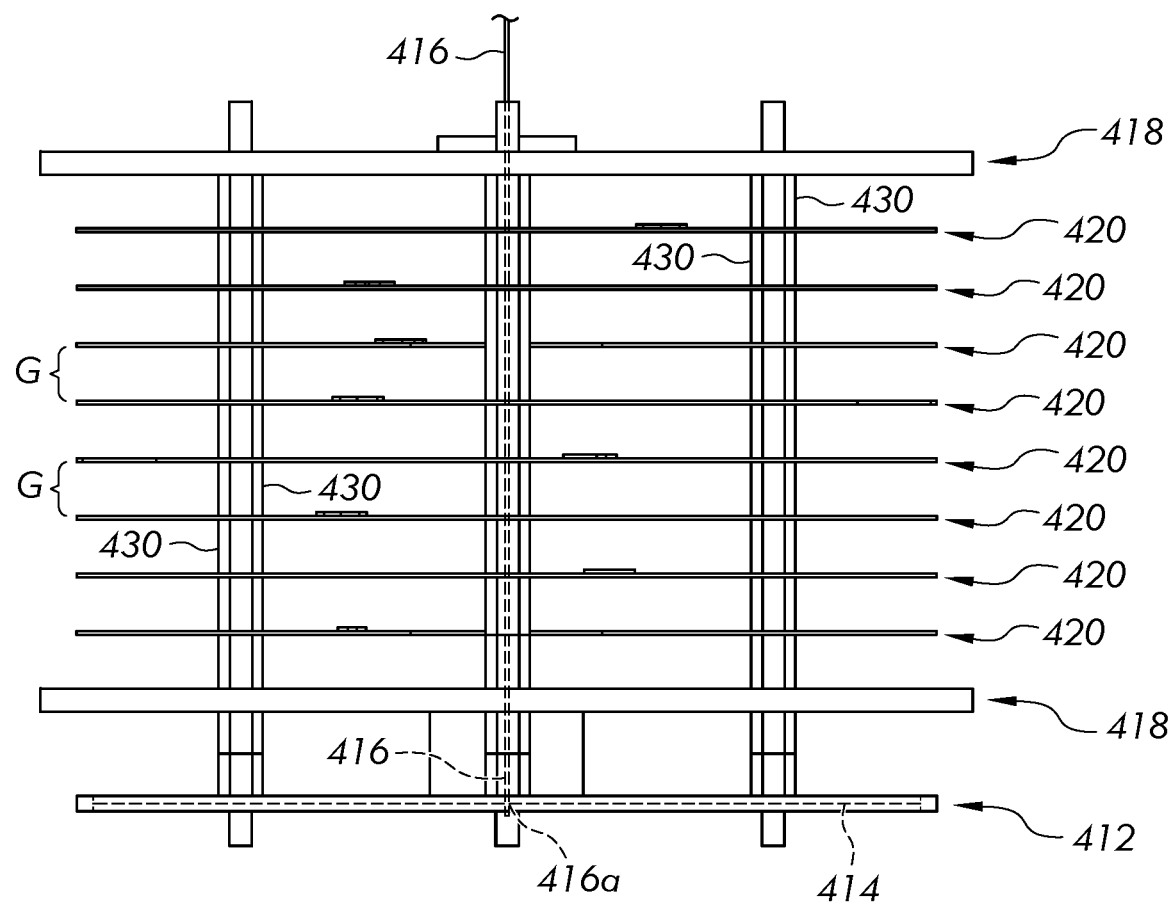
FIG. 10 illustrates a sectioned, side view of the electrostatic precipitator assembly of FIG. 9 in accordance with an example embodiment.

Referring to FIGS. 9 and 10, the ESP plate assembly 410 may include a metallic ring 412, an ionizer wire 416, and a plurality of ESP plates 420 interposed between a pair of end plates 418, i.e., a first end plate 418a and a second end plate 418b. The ESP plates 420 alternate between uncoated ESP plates 421 (cathodes) and coated ESP plates 423 (anodes). In the illustrated embodiment, there are a total of eight ESP plates 420, although it is contemplated that the number of ESP plates 420 may be different without departing from the scope of the present disclosure.

Each ESP plate 420 is preferably made of aluminum, although other metallic materials are also contemplated. The coated ESP plates 423 are preferably coated with a photocatalyst, for example, a crystalline titanium dioxide anatase ("an anatase coating").

As shown in FIG. 10, the plurality of ESP plates 420 are stacked in a parallel arrangement and are spaced apart in an axial direction via spacers 430. In a preferred embodiment, the spacers 430 are insulated to prevent the ESP plates 420 from arcing therebetween when voltage is applied to the ESP plate assembly 410. The spacers 430 also serve to preserve the spatial integrity between the plates 420 when the air cleaning apparatus 200 is operated. Additionally, it is noted that adjacent ESP plates 420 are spaced apart relative to each other based on a gap G. This gap G may be determined based on factors including voltage potential and the sizing of the ESP plates 420.

With reference to FIG. 9, each ESP plate 420 defines a first opening 424 extending between a lower surface 420b and an upper surface 420a thereof. In the illustrated embodiment, the first opening 424 is substantially semi-elliptical shaped and defines an orifice for the passage of air. Yet, in some embodiments, it is contemplated that the first opening 424 may take on other shapes as forms.

In the illustrated embodiment, the first openings 424 are circumferentially offset relative to each other such that air passing through the ESP plate assembly 410 is induced to form a spiral air flow pattern. As noted above, the baffles 308 (FIG. 8) of the air intake 300 (FIG. 8) are configured to direct air to the first opening 424 in the leading ESP plate 421a of the ESP plate assembly 410. In this manner, air entering the first opening 424 of the leading ESP plate 421a follows a path of least resistance defined by the circumferential offset arrangement of the first openings 424 to thereby generate a spiral air flow pattern. It is noted that generating a spiral air flow pattern is particularly beneficial for improving air flow efficiency within the inner shroud 470 and for exposing more air, and particularly the pathogens in the air, to the respective surfaces of the coated ESP plates 423 to achieve a greater reduction of airborne viruses or pathogens, as discussed in detail below.

Still referring to FIG. 9, the ESP plates 420 define a second opening 426 extending between a lower surface 420b and an upper surface 420a thereof for receiving an ionizer wire 416 that is extended therethrough. The ionizer wire 416 is configured to ionize air passing through the ESP plate assembly 410. The ESP plate assembly 410 may optionally include a metallic mesh 414 bounded by a metallic ring 412. In the illustrated embodiment, a first end 416a (FIG. 10) of the ionizer wire 416 is conductively connected to the metallic mesh 414. An opposing, second end (not shown) of the ionizer wire 416 may be connected to the second end plate 418b such that the ionizer wire 416 is tensioned by the first and the second end plates 418a and 418b, e.g., held tightly by the end plates 418.

In operation, a high voltage potential is applied to the ionizer wire (from a power source not shown) to generate ions for ionizing air passing through the inner shroud 470. In particular, the ionizer wire 416 creates an energy equivalent to a band gap energy of anatase disposed on the coated ESP plates 423. In some embodiments, it is contemplated that the power source for supplying power to the ionizer wire 416 is a power source capable of producing 10 kV. It is also contemplated that the ionizer wire 416 may be made from a tungsten material, although other suitable conductive materials are also contemplated.

As noted above, the ESP plates 420 alternate between uncoated ESP plates 421 and coated ESP plates 423. The uncoated ESP plates 421 function as cathodes while the coated ESP plates 423 function as anodes of the ESP plate assembly 410. Power is supplied to the ESP plate assembly 410 from an external power source (e.g., via a 2 kV supply, not shown) to create a voltage differential between the cathodes (i.e., uncoated plates 421) and the anodes (i.e., anatase coated plates 423) when the air cleaning apparatus 200 is being operated. This voltage differential attracts ionized air pathogens and contaminates to the anodes (i.e., anatase coated ESP plates 423), as discussed in detail below.

Turning to FIGS. 7 and 11, the inner shroud 470 of the air cleaning apparatus 200 defines a cylindrical chamber bounded by a circumferential wall 470a. A plurality of first openings 470b may extend through the circumferential wall 470a for the passage of UV-C light. Specifically, a plurality of UV-C light assemblies 490 are mounted to the circumferential wall 470a of the inner shroud 470 for irradiating UV-C light through the respective first openings 470b.

Referring to FIG. 7, each UV-C light assembly 490 may include a holder 494 defining a sleeve or a slot for removably receiving a LED printed circuit board (PCB) 492 therein. In some embodiments, each LED PCB 492 may embody a LED strip including four UV lights (comprising light emitting diodes), although it is contemplated that the number of UV lights and type of UV-C light assemblies may be different without departing from the scope of the present disclosure. In some embodiments, each UV-C light assembly 490 may include a heat sink (not shown) for dissipating heat generated therefrom. In such embodiments, the heat sinks may embody low-profiled heat sinks exposed to an annular space 223 (FIG. 13) defined by the inner shroud 470 and the outer shroud 220, e.g., to thereby cool the heat sinks via air flowing therethrough.

As shown in FIG. 7, the first openings 470b and the UV-C light assembles 490 are spaced apart relative to each other, e.g., 120 degrees relative to each other as shown. This arrangement maximizes the exposure of the coated ESP plates 423 (FIG. 9) to UV-C light irradiated from the UV-C light assemblies 490.

Referring to FIGS. 7 and 9, in operation, the UV-C light assemblies 490 are operable to irradiate the coated ESP plates 423 (FIG. 9) with UV-C light to activate the anatase coating disposed thereon. Concurrently, a voltage is applied to the ionizer wire 416 (FIG. 9) for ionizing air passing through the inner shroud 470. Additionally, a voltage is applied to the ESP plate assembly 410 to establish an electrical field (e.g., between the anodes and cathodes) for attracting ionized air pathogens towards the photoactivated anatase coating disposed on the coated plates 423, i.e., the anodes.

Distinctively, ionized air pathogens contacting the coated plates 423 are inactivated by the photoactivated anatase coating to achieve a high degree of (up to an estimated log 7) reduction of pathogens, i.e., viruses. Specifically, the interaction between the photoactivated anatase and the ionized pathogens produces a reactive oxygen species (ROS) that inactivates or destroys the pathogens.

In the illustrated example, the surfaces 420a and 420b of the coated plates 423 are substantially perpendicular to the air flow induced through the inner shroud 470. This orientation is particularly beneficial for reinforcing the interaction between the ionized pathogens and the coated plates 423, e.g., to reinforce the forces created by an electric field generated by the ESP plate assembly to thereby attract pathogens to the plates.

It is also noted that the UV-C light irradiated from the UV-C light assemblies 490 serve a secondary function for irradiating and destroying residual pathogens on the surfaces of the ESP plates and/or in the air passing through the inner shroud 470.

Referring to FIGS. 7 and 11, the reactor core may optionally include a LED ring 440 arranged rearward of the ESP plate assembly 410. The LED ring 440 is configured to treat air passing through the inner shroud 470 by inactivating residual pathogens that evade treatment from the ESP plate assembly 410.

A filter assembly 450 may be disposed rearward of the LED ring 440 for eliminating ionized air particles and reactive oxygen species (ROS) such as ozone or hydrogen peroxide in the air passing through the inner shroud 470. It is contemplated that the filter assembly 450 may be made of a material such as Ag/Cu or wool.

Figure 12:
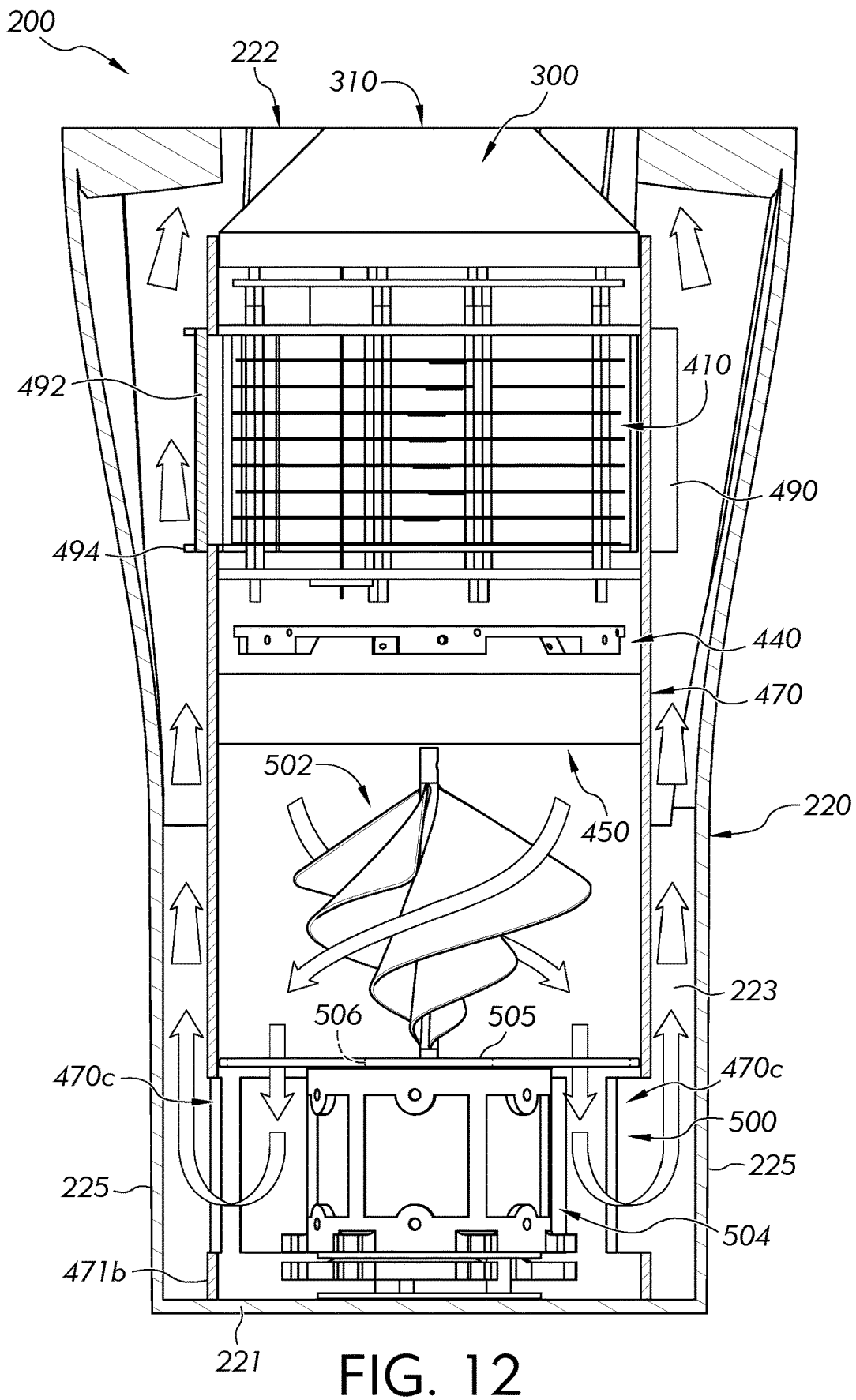
FIG. 12 illustrates a sectioned, side view of the air cleaning apparatus of FIG. 6.

Referring to FIGS. 11 and 12, a plurality of second or egress openings 470c may be formed through the circumferential wall 470a of the inner shroud 470. As shown in FIG. 12, decontaminated or sanitized air exits the inner shroud 470 through the egress openings 470c before entering an annular space 223 located between the inner shroud 470 and the outer shroud 220, as discussed in detail below.

With reference to FIG. 12, the fan assembly 500 is disposed rearward of the filter assembly 450 and is configured to induce air flow through the inlet 310 of the air intake 300, and through the inner shroud 470 to form a spiral air flow pattern, as discussed in detail above. The fan assembly 500 includes a modified Archimedes impeller 502 powered by a high-speed brushless DC electric motor 504 (BLDC motor). In some embodiments, it is contemplated that the BLDC motor 504 is configured to operate up to 30,000 revolutions per minute. Although, it is noted that the speed of the motor may change depending on the required cleaning capacity of the air cleaning apparatus. For instance, the speed of the motor may operate at a lower speed if a patient situated below the air cleaning apparatus is moved or discharged, thereby obviating a need for a high speed, i.e., a higher and more focused extraction rate. In such embodiments, the speed of the fan may operate at a low speed to enable the air cleaning apparatus to still perform its cleaning function, for example, in a standby mode until a new patient is placed beneath the air cleaning apparatus. In other examples, it is contemplated that the motor may operate at a low speed when there are no people in a room, for example, when the air cleaning apparatus is utilized in a commercial establishment such as a business meeting room or a restaurant.

Referring to FIGS. 7 and 12, the BLDC motor 504 of the illustrated embodiment includes a flange 505 defining a plurality of openings 506 for the passage of air. These openings 506 allow air to pass through the flange 505 prior to exiting the inner shroud 470 through the egress openings 470c of the inner shroud 470. Although it should be appreciated that the motor (or mounting arrangement thereof) may be different in other embodiments, e.g., may not include a flange with openings. As shown in FIG. 12, a second or rear end 471b of the inner shroud 470 abuts against a rear wall 221 of the outer shroud 220 such that air passing through the inner shroud 470 is forced to exit the inner shroud 470 through the egress openings 470c of the inner shroud 470. Air exiting the inner shroud 470 impinges a side wall 225 of the outer shroud 220, whereupon the air is redirected toward a front of the air cleaning apparatus 200 through the annular space 223 between the inner shroud 470 and the outer shroud 220.

Figure 13:
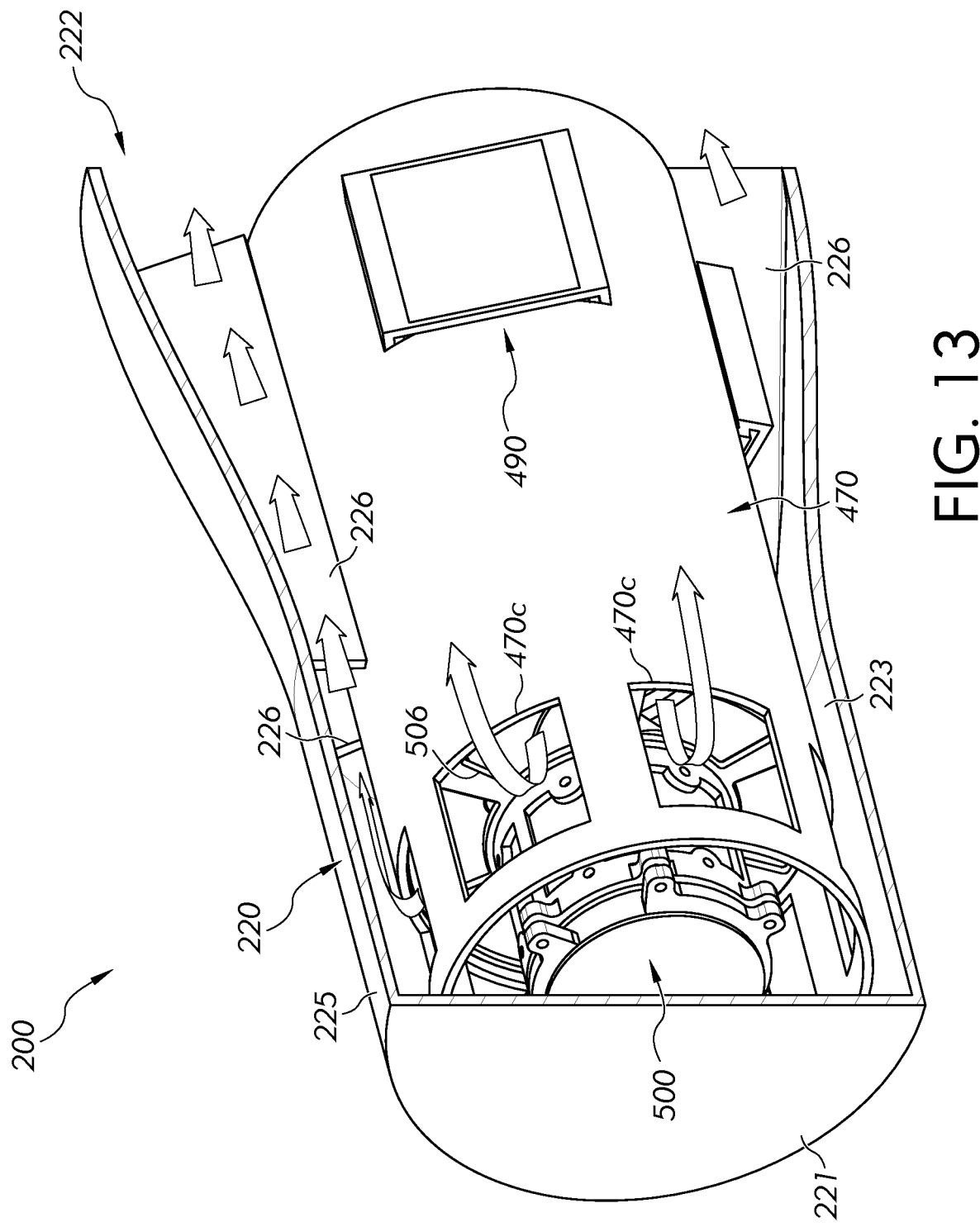
FIG. 13 illustrates a sectioned, perspective view of an outer shroud for an air cleaning apparatus shown in relation to an inner shroud in accordance with an example embodiment.

Referring to FIGS. 7 and 13, the outer shroud 220 embodies a substantially cylindrical shaped structure with a diameter that generally increases from the rear wall 221 thereof toward a front end 227 thereof proximate an opening 222 of the outer shroud 220. The outer shroud 220 defines an internal chamber for accommodating the inner shroud 470 and the reactor core 400 therein. In some embodiments, it is contemplated that spacers may position the inner shroud 470 within the outer shroud 220 to ensure that the inner shroud 470 and the outer shroud 220 are positioned coaxially relative to a longitudinal axis LA (FIG. 7) of the air cleaning apparatus 200, e.g., such that the inner shroud and the outer shroud are disposed in a concentrical arrangement. In some embodiments, baffles extending from an inner surface of the outer shroud may accomplish this spacing function.

In the illustrated embodiment, an inner surface 224 of the outer shroud 220 includes a plurality of baffles 226 arranged thereon extending in a longitudinal direction. It is contemplated that the baffles 226 may be integrally formed with the outer shroud, e.g., via a molding, welding, or via adhesion. It is also contemplated that the baffles 226 may be removably attached to the inner surface 224 of the outer shroud 220 via removable fasteners and the like.

The baffles 226 extend longitudinally and are skewed relative to the longitudinal axis LA (FIG. 7) of the air cleaning apparatus 200. In this respect, the baffles 226 are configured to direct air flowing toward the front end 227 of the outer shroud 220 to flow at an acute angle relative to the longitudinal axis LA (FIG. 7). This interaction between the baffles 226 and the air induces the air to form a spiral air flow pattern or vortex (FIG. 13) for generating an area of negative pressure in front of the air cleaning apparatus 200, e.g., extending in front of the air cleaning apparatus for an extended distance therefrom. This enables the air cleaning apparatus to extract contaminated air from a targeted area extending in front of the air cleaning apparatus 200 (or below depending on the specific orientation thereof).

This aspect of the present disclosure is particularly advantageous for extracting contaminated air from localized regions (e.g., near an infected patient's nose, mouth, or face) and sanitizing the contaminated air (e.g., via the reactor core 400) to create sanitized air which is expelled to an external environment through a front opening 222 (FIG. 13) of the outer shroud 220, while creating a vortex for extracting additional contaminated air into the air cleaning apparatus 200.

In this manner, it is contemplated that the air cleaning apparatus 200 may be arranged in specific locations where high efficiency and targeted extraction is needed. Moreover, the targeted extraction described herein is particularly beneficial for decontaminating air by neutralizing a high degree of airborne viruses (e.g., through the reactor core 400 as discussed above) in areas of high risk, e.g., in an ICU.

In some embodiments, it is contemplated that the inner components of the air cleaning apparatus 200 may be provided as removable or replacement components. For example, it is contemplated that the inner shroud, the ESP plate assembly, the filter assembly, and/or the UV-C light assemblies and the LED rings may be removably mounted within or on the inner shroud to allow for an efficient means for cleaning and/or replacing these components as needed.

The described air cleaning apparatus is a versatile, efficient, and cost-effective way to treat air and reduce transmission of airborne viruses, such as COVID-19, between infected patients and treating providers in a way that is far superior to current strategies of HEPA air filtration or excessive dependence on PPE for exposure prophylaxis. In addition, by minimizing the risk of transmission between groups of people through real time air purification, the air cleaning apparatus helps provide a return to normalcy during a pandemic by giving people peace of mind that they are safe from infection in enclosed spaces.

While a specific stand-alone design and configuration of an air cleaning apparatus has been shown and described herein, it is to be appreciated that the technology can be used in various other configurations for extracting contaminated air from a targeted area. As an example, various different configurations for an air cleaning apparatus are illustrated in the figures and can be dependent on the size of the target area and/or on the particular application. For instance, the technology may be integrated into a fan intake of an existing system, such as an HVAC system, for a targeted environment. The air cleaning apparatus can be integrated into or mounted on a robot that allows the system to move in and out of spaces (ICUs, hospital rooms) to decontaminate multiple areas. The air cleaning system can be scaled to a personal size and configured within a device that forms a seal over a patient's face/mouth/breathing tube and allows for real time extraction and decontamination of infected air during intubation or extubation. The air cleaning apparatus can be integrated into overhead fixtures, such as lighting fixtures, which serve as a fan intake to be used overhead in restaurants, conference rooms, public transportation (trains, buses, planes), office cubicles. The air cleaning apparatus can be integrated into personal, military, and/or commercial vehicles. Moreover, the air cleaning apparatus can be coupled with various other technologies, as desired. For instance, the air cleaning apparatus can be coupled with airborne pathogen biosensors, with or without mounting on a robot, to allow active surveillance and decontamination of enclosed spaces with potential bioterrorism threats during military operations.

The air cleaning apparatus described herein is effective to neutralize and deactivate airborne pathogens in real time rather than accumulate the pathogens on filters which are fomite vectors for viral spread or requiring rooms to be vacated before sterilization can occur. If desired, the air cleaning apparatus can work independently of blowers and HVAC systems, which often scatter the airborne pathogens across the enclosed area. Treated air will be recirculated into the room as newly infected air is extracted through the reactor core 100. The design of the fan 45 is configured to extract at least 2 times, and preferably up to 5 times more infected air compared to existing ventilation systems without need for integration into HVAC systems. This allows flexibility to move the air cleaning apparatus 10 as needed to clean and sanitize air in the area of highest infectivity regardless of the geometry of the target space. The air cleaning apparatus 10 can reduce viral load and the risk of transmission in a more efficient and cost-effective way than existing technologies.

The air cleaning apparatus described herein can be used in various settings in which air cleaning and sanitization is desired, including, but not limited to:

Hospital ICUs
Hospital operating theaters or ambulatory surgical centers
Imaging facilities (CT, MRI) to allow improved turnover between patients who are COVID+/respiratory pathogen illness+
Dental clinics
Urgent cares
COVID or infectious disease testing facilities
Assisted living facilities or retirement homes
Restaurants (fan intake as a lighting fixture above the table)
Conference Rooms
Public transportation systems (Amtrak, buses, urban metro)
Individual units over office cubicles
Residential homes where can be used as a standalone unit in the house or integrated into the air conditioning or central air systems
For use in military reconnaissance and decontamination missions (use in tanks as mentioned above, mounted on robots for threat assessment and remote decontamination)

Numerous embodiments have been described herein. It will be apparent to those skilled in the art that the above methods, architecture, and apparatuses may incorporate changes and modifications without departing from the general scope of this invention. It is intended to include all such modifications and alterations as far as they come within the scope of the appended claims or the equivalents thereof.

What is claimed is:

1. A method for disinfecting an airstream containing microorganisms by electrostatic precipitation by passing the airstream through the space between at least one grounded collection plate having at least one electrode spaced apart therefrom connected to a source of electric potential, wherein the method comprises:
   extracting the airstream from a targeted area by creating a vortex of negative pressure above the targeted area;
   contacting the airstream with a photocatalyst having a predetermined band gap energy coated on the surface of each grounded collection plate and illuminated with photons having a wavelength corresponding to the band gap energy of the photocatalyst, so that at least a portion of the microorganisms that collect on the grounded collection plate are destroyed by photocatalytic oxidation.

2. The method of claim 1, wherein the airstream is extracted using a combination of high-speed air suctioning fans and aerodynamically shaped intake funnel creating a conical vortex of air that extends about 6 feet deep and 6 feet wide.

3. An air cleaning apparatus comprising:
   a housing;
   a fan configured to extract an airstream from a targeted area and into the housing;
   an electrostatic precipitator positioned upstream of the fan and configured to filter particulates greater than 10 microns in size; and
   a bank of UV-C light emitting diodes removably attached to the housing,
   wherein the electrostatic precipitator includes at least one plate coated with a film of photocatalytic titanium dioxide nanoparticles,
   wherein photo-activation of said film predominantly in an Anatase phase structure is performed by an envelope of UV-C radiation generated by said bank of UV-C light emitting diodes which evenly distributes radiation across said at least one plate in proximity.

4. The air cleaning apparatus of claim 3, wherein an internal part of the housing is internally serrated with aerodynamic features to retain the vortices until a point of exit from the housing.

5. The air cleaning apparatus of claim 3, wherein the airstream travels within a UV radiation zone in close proximity of the bank of UV-C light emitting diodes to neutralize any remaining pathogenic particles in the airstream.

6. The air cleaning apparatus of claim 3, further comprising: a sponge scrubber positioned near an outlet of the housing, the sponge scrubber comprising oxidizable metals to remove residual reactive oxygen species; and a passive adsorption filter to filter at least one of VOCs and anesthesia gases.

7. The air cleaning apparatus of claim 3, further comprising a plurality of laser diode based pointers coupled to the housing to facilitate positioning and alignment of the housing.

8. The air cleaning apparatus of claim 3, further comprising a five-degree-of-freedom wall mounted or floor mounted arm that positions the housing in place, wherein the arm includes a conduit configured to receiving power lines therethrough.

9. The air cleaning apparatus of claim 3, wherein said electrostatic precipitator includes a first plate and a second plate, wherein said first and second plates are spaced from one another via a spacer, and wherein said spacer is insulated to prevent the first and second plates from arcing.

* * * * *